Figure 1:
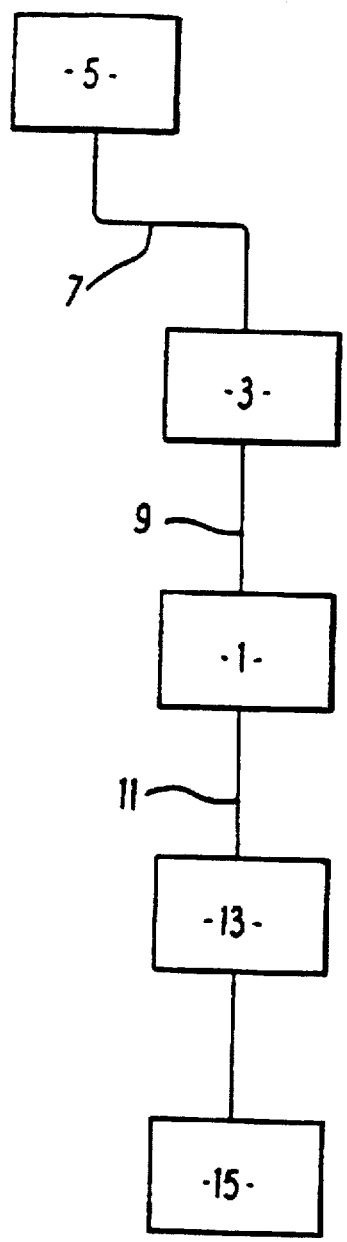

United States Patent [19]

Smart

[11] Patent Number: 5,750,081

[45] Date of Patent: May 12, 1998

[54] SOLVENT EXTRACTION OF METAL CONTAINING SPECIES

[75] Inventor: Neil Graham Smart, Preston, United Kingdom

[73] Assignee: British Nuclear Fuels plc, Warrington, England

[21] Appl. No.: 571,846

[22] PCT Filed: Apr. 20, 1995

[86] PCT No.: PCT/GB95/00891

§ 371 Date: Jan. 31, 1996

§ 102(e) Date: Jan. 31, 1996

[87] PCT Pub. No.: WO95/28999

PCT Pub. Date: Nov. 2, 1995

[30] Foreign Application Priority Data

Apr. 21, 1994 [GB] United Kingdom ............ 9407892

[51] Int. Cl.$^6$ .................................................. C01G 56/00
[52] U.S. Cl. .................................. 423/3; 423/8; 210/634; 405/128; 134/2; 134/25.1; 976/DIG. 392; 976/DIG. 376
[58] Field of Search ............... 423/3, 8; 210/634; 405/258, 128; 976/DIG. 392, DIG. 376; 134/2, 25.1

[56] References Cited

U.S. PATENT DOCUMENTS

| | | |
|---|---|---|
| 2,830,066 | 4/1958 | Magnusson . |
| 4,518,484 | 5/1985 | Mann ............................. 208/87 |
| 5,085,834 | 2/1992 | Lemaire et al. ................. 423/8 |
| 5,225,173 | 7/1993 | Wai ................................. 423/2 |
| 5,322,644 | 6/1994 | Dunn et al. ................... 252/626 |
| 5,356,538 | 10/1994 | Wai et al. ................... 210/634 |

FOREIGN PATENT DOCUMENTS

| | | |
|---|---|---|
| 0282810 | 9/1988 | European Pat. Off. ...... G21C 19/46 |
| 0550211 | 7/1993 | European Pat. Off. ...... G21F 9/00 |

*Primary Examiner*—Ngoclan Mai
*Attorney, Agent, or Firm*—Sheridan Ross P.C.

[57] ABSTRACT

A method of extracting metal species from a metal species containing medium which comprises contacting the medium with an extractant solvent which comprises a supercritical fluid and a complexant for solubilizing metal species in the said medium and also a conditioning agent for changing the oxidation state of the metal species.

11 Claims, 1 Drawing Sheet

SOLVENT EXTRACTION OF METAL CONTAINING SPECIES

The present invention relates to the solvent extraction of metal containing species.

Solvent extraction of metal containing species is used in a variety of analytical and industrial applications particularly in the chemical engineering and waste treatment fields. For example, hazardous radioactive and non-radioactive species present in a solid or liquid medium may be extracted into a solvent system and subsequently isolated and disposed of or recycled as appropriate.

A known technique which has been used for solvent extraction of metal containing species is supercritical fluid extraction (SFE). This technique is reported in a number of papers for example:

Hawthorne, S B Anal. Chem. 1990, 62, 633A; Fahmy, T M; Paulaitis, M E; Johnson, D M; McNally, M E P Anal. Chem. 1963, 65, 1462; Lin, Yuehe; Brauer, R D; Laintz, K E; Wai, C M Anal. Chem. 1993, 65, 2549; and Hedrick, J L; Mulcahey, L J Taylor L T. In "Supercritical Fluid Technology—Theoretical and Applied Approaches to Analytical Chemistry", Bright F V and McNally M E, Eds.; ACS Symposium Series 488; Amer. Chem. Soc., Washington, D.C., 1991, p 206–220. In SFE the extractant solvent comprises a supercritical fluid such as carbon dioxide together with a complexant or chelant which serves to dissolve the metal species by forming a soluble complex.

According to the present invention there is provided a method of extracting metal species from a metal species containing medium which comprises contacting the medium with an extractant solvent which comprises a supercritical fluid and a complexant for solubilising metal species in the said medium and also a conditioning agent for changing the oxidation state of the metal species.

The conditioning agent may comprise an oxidising agent or a reducing agent and is present to assist dissolution of the metal species in the complexant by changing the oxidation state of the metal species. The presence of the conditioning agent thereby beneficially increases the efficiency of the solvent system in dissolving the metal species.

Where the conditioning agent is an oxidising agent it may be selected from a peroxide such as $H_2O_2$, a perchlorate such as $NaClO_3$, oxygen, ozone and potassium permanganate or a plurality of oxidising species.

Where the conditioning agent is a reducing agent it may be selected from hydrogen, hydrazine or a solution containing an oxidisable metal species such as $Fe^{++}$ or $Cu^+$, or a plurality of reducing species.

The medium from which metal species is desired to be removed by the method according to the present invention may be a solid or liquid medium. Where the medium is a solid it may comprise a particulate material such as soil, sludge, an industrial process residue, an industrial process slag or the like. The metal species may be contained on the surface of the particles and/or bound within the particles. The medium could alternatively be a material to be decontaminated, eg a metal or concrete structure, waste building materials such as rubble or contaminated waste materials such as rubber, plastics or textiles materials. Where the medium is a liquid it may for example comprise a process solvent or an industrial effluent stream.

The method of the present invention may for example be employed to analyse the concentration of metal species of interest in liquid or solid samples. For example, when analysing for the presence of contaminants it may be desirable to produce a stock solution which is subsequently divided into multiple samples for different analyses.

The present invention may alternatively be employed to decontaminate surfaces contaminated with radioactive or non-radioactive toxic heavy metal species.

The present invention may for instance be employed for soil clean-up for land remediation purposes.

The present invention may alternatively be employed in processes which employ conventional solvent extraction, eg dissolution of actinides in reprocessing of irradiated nuclear fuel or dissolution of uranium in the refinement treatment of uranium ores.

The metal species to be extracted by the method of the present invention may comprise radioactive species which may include:

(i) actinides or their radioactive decay products or compounds thereof;

(ii) fission products;

(iii) heavy metals or compounds thereof.

Actinides are elements having periodic numbers in the inclusive range 89 to 104.

The term 'fission product' as used herein refers to those elements formed as direct products (or so-called 'fission fragments') in the fission of nuclear fuel and products formed from such direct products by beta decay. Fission products include elements in the range from selenium to cerium including elements such as $_{56}Ba$, $_{40}Zr$ and $_{52}Te$ $_{55}Cs$ and $_{58}Ce$.

The metal species to be extracted by the present invention may alternatively comprise non-radioactive heavy metal species. Non-radioactive heavy metals desired to be separated by the method of the present invention include toxic metals such as cobalt, chromium, lead, cadmium and mercury which are commonly found as earth contaminants near industrial plants and on waste disposal sites and in aquatic sediments employing chemicals containing those elements.

The complexant employed in the method according to the present invention is selected according to the metal species to be extracted. Desirably, the complexant has high volatility and has a significant change in solubility in the supercritical fluid with temperature. This allows the complexes to be formed to be separated from the solvent by known processes such as precipitation.

For example, for the extraction of metals such as mercury, lead and cadmium, fluorinated dithiocarbamates are known to be suitable complexants. For the extraction of actinides such as uranium and thorium fluorinated β-diketones are known to be suitable complexants; and for actinides and lanthanides crown ethers are suitable.

The aforementioned complexants generally comprise negatively charged ligands. The complexant may comprise a plurality of such ligands. It may also include as an optional additive one or more neutral ligands, such as an organic phosphate, eg tributyl phosphate.

In the method according to the present invention the composition comprising the solvent mixture may include in the following relative proportions:

(a) supercritical fluid, from 80 to 99.99 per cent by volume;

(b) complexant, from 0.01 to 10 per cent by volume;

(c) conditioning agent, from 0.01 to 10 per cent by volume.

Further optional additives may be included in the extractant solvent. For example, minor aqueous additives such as water (up to 10 per cent by volume of the mixture with components (a), (b) and (c) above) and minor organic additives such as ethanol may be included in the solvent up to 10 per cent by volume.

In the method according to the present invention the complexant and the conditioning agent may each be added to the supercritical fluid at any time prior to or during contacting of the metal containing species. For example, complexant and conditioning agent may be separately formed into an extractant mixture and then added to supercritical fluid in an extractant vessel and the extractant solvent so formed may be passed along a tube or pipe under pressure to a contactor in which the medium to be treated is contacted. The metal containing solution may be further transported to an extractor in which the metal species is separated from the solution by precipitation. The extractor may for example comprise a collector vessel having associated means for changing the pressure and/or temperature of the supercritical fluid-containing solution whereby the metal species therein are precipitated. The collector vessel may contain an organic solvent eg chloroform. The precipitate may subsequently be separated in a known way eg by filtration, centrifugation, flocculation or by use of a hydrocyclone or other known means.

The actinides and other hazardous material may thereby be obtained in highly concentrated form. If desired, particular actinides such as plutonium can be further separated from the other separated species in a known way eg as conventionally employed in irradiated nuclear fuel reprocessing methods. High activity level radioactive elements separated may be encapsulated in a known way eg by a known vitrification process. In any event, all procedures for handling concentrated plutonium and other hazardous elements are carried out by remote operations in radiation shielded enclosures.

The extraction of metals by the method according to the present invention may beneficially be carried out by using chemicals which are not themselves harsh to the environment and without substantial production of secondary aqueous waste streams as in the prior art.

Embodiments of the present invention will now be described by way of example with reference to the accompanying drawing, in which:

FIGURE 1 is a flow chart of a supercritical fluid extraction process embodying the present invention.

As illustrated in FIGURE 1 actinide-contaminated particulate material such as sand is washed, rinsed and air dried and placed in a stainless steel container in a commercially available contactor vessel 1. A extractant comprising a mixture of a complexant fluorinated β-diketone, eg hexafluoroacetylacetone and an oxidising agent eg $H_2O_2$, provided in equal proportions, is formed in a high pressure extractant cylinder 3. The contactor vessel 1 and extractant cylinder 3 are placed in an oven and heated to an accurately controlled temperature of 60° C. Supercritical $CO_2$ at a pressure of 150 atmospheres is passed from a source 5 via a fused silica tube 7 into the vessel 3 where it is mixed with the extractant.

The supercritical fluid-containing extractant solvent is passed via a further tube 9 through the particulate material in the vessel 1 and actinide ions are thereby oxidised and dissolved. The solution so formed is passed via a tube 11 to an extractor 13 in which the pressure of the supercritical fluid is reduced to one atmosphere and actinide eg uranium or plutonium particles are precipitated. The actinide particles are thereafter separated eg by filtration in a separator 15 and the filtrate is encapsulated and disposed of safely in a known manner.

I claim:

1. A method of extracting metal species from a metal species containing medium which comprises contacting the medium with an extractant solvent which comprises a supercritical fluid and a complexant for solubilising metal species in the said medium and also a conditioning agent for changing the oxidation state of the metal species.

2. A method as in claim 1 and wherein the conditioning agent comprises an oxidising agent or a reducing agent and is present to assist dissolution of the metal species in the complexant by changing the oxidation state of the metal species.

3. A method as in claim 1 and wherein the medium is a solid and comprises a particulate material comprising soil, sludge, an industrial process residue or an industrial process slag.

4. A method as in claim 1 and wherein the medium is a solid material to be decontaminated and comprises a metal or concrete structure, waste building materials, rubble or contaminated waste materials.

5. A method as in claim 1 and wherein the medium is a liquid and comprises a process solvent or an industrial effluent stream.

6. A method as in claim 1 and wherein the method is employed for soil clean-up for land remediation purposes.

7. A method for land remediation, comprising contacting soil having metal species therein with an extractant solvent which comprises a supercritical fluid and a complexant for solubilizing metal species in the soil and providing a reducing agent for changing the oxidation state of the metal species.

8. A method as set forth in claim 1, wherein the medium from which metal species is desired to be removed comprises a solid or liquid medium.

9. A method as set forth in claim 1 which is employed to analyze the concentration of metal species in a liquid or solid sample.

10. A method as set forth in claim 1 wherein the method is employed to decontaminated surfaces contaminated with radioactive or non-radioactive toxic heavy metal species.

11. A method as set forth in claim 1, wherein the composition comprising the solvent mixture includes in the following relative proportions:

(a) supercritical fluid from 80–99.99 percent by volume;
(b) complexant, from 0.01–10 percent by volume; and
(c) conditioning agent, from 0.01–10 percent by volume.

* * * * *